(12) United States Patent
Su et al.

(10) Patent No.: US 7,339,681 B2
(45) Date of Patent: Mar. 4, 2008

(54) SURFACE PLASMON RESONANCE MICROSCOPE USING COMMON-PATH PHASE-SHIFT INTERFEROMETRY

(75) Inventors: Yuan Deng Su, Tainan (TW); Shean Jen Chen, Jhongli (TW)

(73) Assignee: Phalanx Biotech Group, Inc., Hsinchu (TW)

( * ) Notice: Subject to any disclaimer, the term of this patent is extended or adjusted under 35 U.S.C. 154(b) by 192 days.

(21) Appl. No.: 11/288,274

(22) Filed: Nov. 29, 2005

(65) Prior Publication Data

US 2006/0119859 A1 Jun. 8, 2006

(30) Foreign Application Priority Data

Dec. 2, 2004 (TW) ............................... 93137200 A

(51) Int. Cl.
*G01B 11/02* (2006.01)
(52) U.S. Cl. ...................................................... 356/491
(58) Field of Classification Search ................ 356/491, 356/495
See application file for complete search history.

(56) References Cited

U.S. PATENT DOCUMENTS

| | | | |
|---|---|---|---|
| 5,856,873 A * | 1/1999 | Naya et al. ................. 356/369 |
| 5,907,408 A * | 5/1999 | Naya et al. ................. 356/445 |
| 5,917,608 A * | 6/1999 | Naya et al. ................. 356/445 |
| 5,926,284 A * | 7/1999 | Naya et al. ................. 356/445 |
| 2005/0053974 A1* | 3/2005 | Lakowicz et al. ............. 435/6 |
| 2005/0118731 A1* | 6/2005 | Salafsky ..................... 436/518 |
| 2006/0119859 A1* | 6/2006 | Su et al. ..................... 356/495 |
| 2007/0159633 A1* | 7/2007 | Yin et al. ................... 356/445 |
| 2007/0166763 A1* | 7/2007 | Ho et al. ..................... 435/7.1 |

* cited by examiner

*Primary Examiner*—Patrick Connolly
(74) *Attorney, Agent, or Firm*—Volentine & Whitt, PLLC

(57) ABSTRACT

The present invention integrates the surface plasmon resonance and common-path phase-shift interferometry techniques to develop a microscope for measuring the two-dimensional spatial phase variation caused by biomolecular interactions on a sensing chip without the need for additional labeling. The common-path phase-shift interferometry technique has the advantage of long-term stability, even when subjected to external disturbances. Hence, the developed microscope meets the requirements of the real-time kinetic studies involved in biomolecular interaction analysis. The surface plasmon resonance microscope of the present invention using common-path phase-shift interferometry demonstrates a detection limit of $2\times10^{-7}$ refractive index change, a long-term phase stability of $2.5\times10^{-4}\pi$ rms over four hours, and a spatial phase resolution of $10^{-3}$ $\pi$ with a lateral resolution of 100 μm.

18 Claims, 6 Drawing Sheets

SURFACE PLASMON RESONANCE MICROSCOPE USING COMMON-PATH PHASE-SHIFT INTERFEROMETRY

BACKGROUND OF THE INVENTION

1. Field of the Invention

The present invention relates to a surface plasmon resonance (SPR) microscope using common-path phase-shift interferometry and, more particularly, to a microscope which combines SPR and modified common-path phase-shifting interferometry to measure the spatial phase variation caused by bio-molecular interactions upon a sensing chip.

2. Description of the Related Art

As shown in FIG. 1, a surface plasmon wave (SPW) is a physical phenomenon existing in the interference between a metal layer (an Au layer or an Ag layer in the visible light region) and a nonconductive dielectric medium (air or water). Free electrons between the metal film 12 and dielectric medium 13 have collective resonance oscillations along the interface excited by that incident light 14 which is coupled to the metal film 12 through a coupler 11 (a prism). This free electron oscillation is called the SPW.

A method of attenuated total reflection (ATR) is used to excite the free electrons to emit the non-radioactive SPW. That is, p-wave light parallel to the incident plane arrives in the dielectric medium 13 after the total internal reflection of the incident light 14 occurs thereon. The air 13 penetration depth of the p-wave is roughly a half of a wavelength, and therefore the incident light in the interference is also called an evanescent wave. The SPW fluctuates perpendicularly to the interference between the metal film 12 and dielectric medium 13, and it simultaneously propagates along the interference. As a result, and in addition to electromagnetic fields effectively concentrating in the interference, the electric field of the evanescent wave has a maximum value of intensity also existing therein. The intensity exponentially decreases in proportion to the distance from the interference. The SPR is an optical phenomenon in which incident P-wave light excites an SPW such that it reaches a resonance condition. Excitation of the SPR occurs when the wave vectors' parallel component of the incident light, $k_x$, and the wave vector of the SPW, $k_{sp}$, satisfy the following matching condition:

$$k_x = k_0 \sqrt{\epsilon_0} \sin\theta = k_{sp};$$

where $\theta$ is the incident angle of the light, $k_0 = 2\pi/\lambda$ and $\epsilon_0$ is the wavelength dependent dielectric constant of the coupler 11. The wave vector of the SPW is regarded as a dispersion index and can be approximated by:

$$k_{sp} = k_0 \left(\frac{\epsilon_1 \epsilon_2}{\epsilon_1 + \epsilon_2}\right)^{\frac{1}{2}};$$

where $\epsilon_1$ and $\epsilon_2$ are the wavelength dependent complex dielectric constants of the metal film 12 and dielectric medium 13, respectively. When this matching condition is satisfied, most of the incident light energy is transferred to the surface plasmon, i.e. most of the incident light is absorbed by the excitation of the SPW. This phenomenon results in an attenuated reflected spectrum.

SPR biosensors can be applied to measure tiny variations in the dielectric constant or thickness of biomolecular materials at the interface without the need for additional labeling. The SPR technique has been widely applied to biomolecular interaction analysis (BIA). In addition to its inherent convenience, economy, and speed, on-going developments of the SPR technique are aimed at further enhancing its sensitivity, resolution and reliability in order to support the implementation of high-throughput screening processes.

Conventionally, SPR imaging systems apply a parallel monochromatic light beam oriented such that it incidents on a gold film through a prism or a grating-coupling. The angle of incidence is adjusted such that it is close to the SPR angle and the resulting SPR intensity pattern is detected by a CCD (charge coupled device) camera. Although this system has a high-throughput screening capability, its resolution is too low to permit the detection of biomolecules of low molecular weight or low concentration. Of the various SPR detector configurations, applying a prism-coupling to produce optical interference between the SPR phase and the reference light beam produces the best resolution. The current authors previously developed an SPR phase imaging system for the high-throughput real-time dynamic measurement of biomolecular interactions by detecting the variation in the dielectric constant or the thickness of the biomolecular material. However, in common with other SPR phase imaging systems, the developed system was unable to satisfy the strict demands of real-time BIA kinetic studies because it lacked long-term stability. Hence, the current study develops an SPR imaging system with long-term stability and high-resolution capabilities.

SUMMARY OF THE INVENTION

An objective of the present invention is to provide an SPR microscope which uses common-path phase-shift interferometry to solve the phase drift problem resulting from external environmental variety, mechanical vibration, and light source fluctuation. The microscope is suitable for measuring the 2-dimensional variation of the phase perpendicular to the surface of an analyte.

To achieve the objective, the present invention discloses an SPR microscope using common-path phase-shift interferometry. The microscope is employed to have a 2-dimensional phase variation diagram by means of phase reconstruction. The SPR microscope is comprised of a coherent light source, a coupler, an electro-optic modulator and an image camera, wherein a surface of the coupler is overlaid with at least a metallic layer. The coherent light source emits coherent light into the coupler to excite the metallic layer to generate SPW. Only incident P-wave light can induce SPW to reach a resonance condition. Minor variations upon the surface on the metal layer cause the SPR to sharply change the phases of reflective light. Furthermore, the S-wave light is regarded as reference light because its phase remains the same. The electro-optic modulator is employed to have phase-shift interference between the S-wave light and P-wave light, and the image camera captures the corresponding interference pattern.

A liquid crystal phase retarder can act as the electro-optic modulator which has the P-wave light fluctuating along a fast axis and the S-wave along a slow axis. The phase delay of the S-wave light is modulated by the external voltage applied to the modulator to change the direction of its polarization axis. After modulation, the P-wave and S-wave are sent through a polarizer, and then interference between them occurs simultaneously. Finally, the image camera captures the corresponding interference diagrams.

By means of changing the external voltage, the phase difference between the fast and slow axes also varies. The various interference diagrams are obtained from phase differences. A continuous distribution diagram of phase variation is then reconstructed from the several interference diagrams using a phase reconstruction method.

BRIEF DESCRIPTION OF THE DRAWINGS

The invention will be described according to the appended drawings in which.

PREFERRED EMBODIMENT OF THE PRESENT INVENTION

Figure 1:
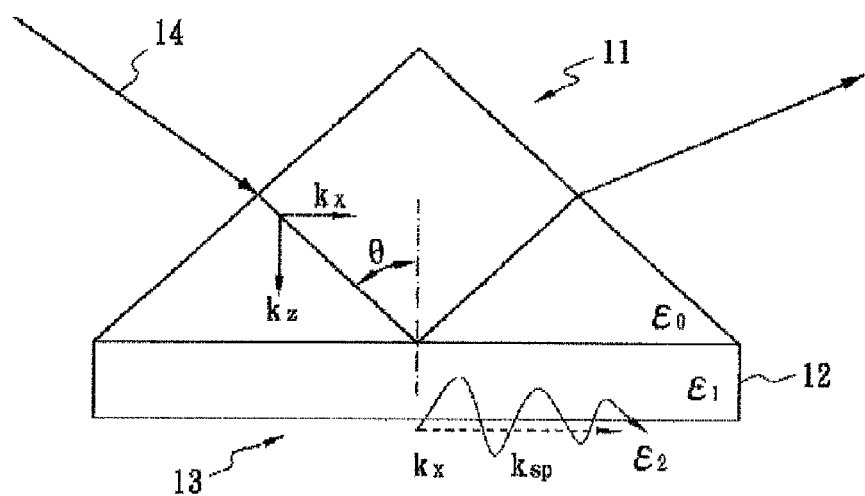
FIG. 1 is a schematic diagram of a Kretschmann-type SPR sensor.
Figure 2:
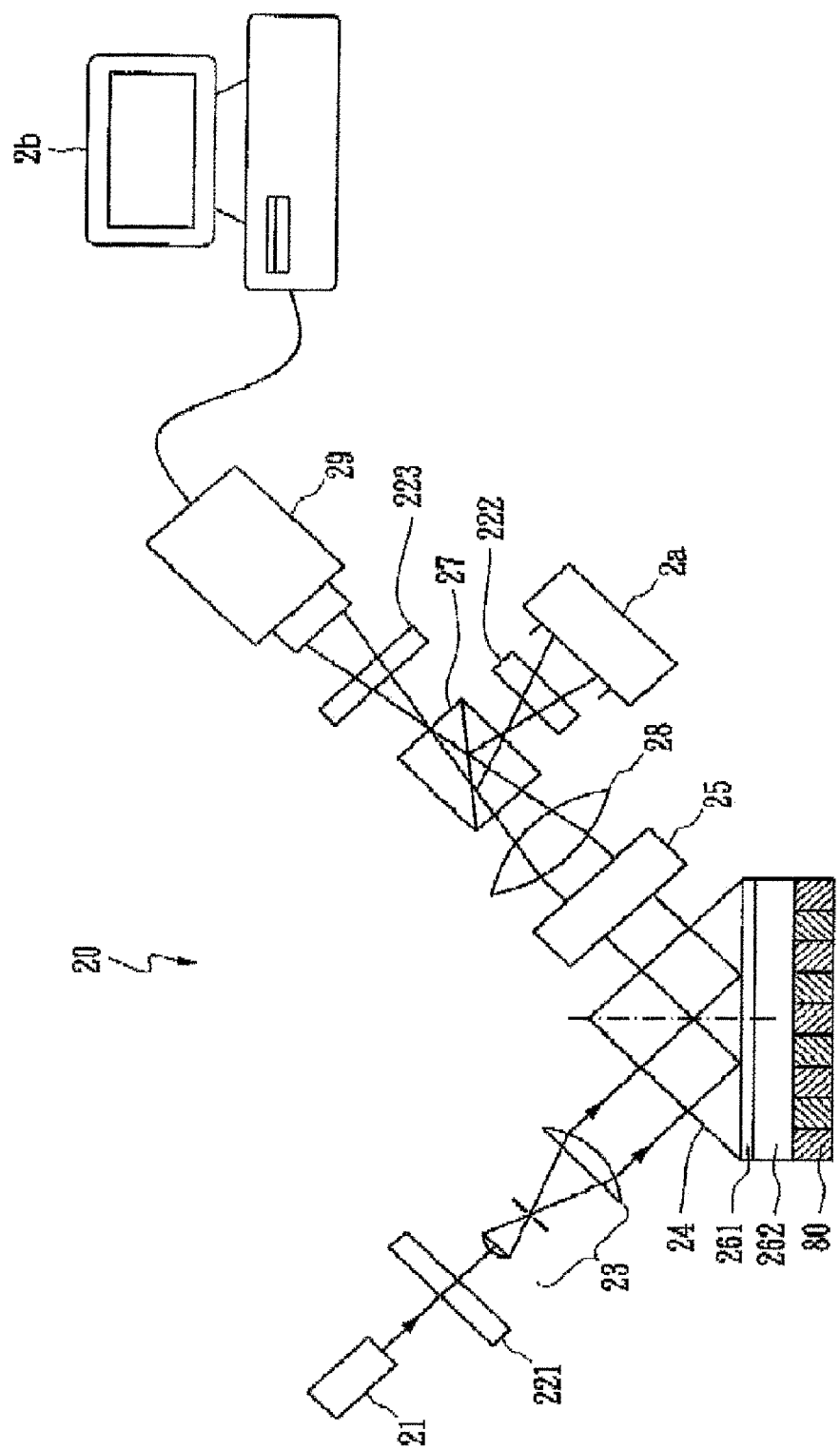
FIG. 2 is a schematic diagram of an SPR microscope using common-path phase-shift interferometry in accordance with the present invention.
Figure 3:
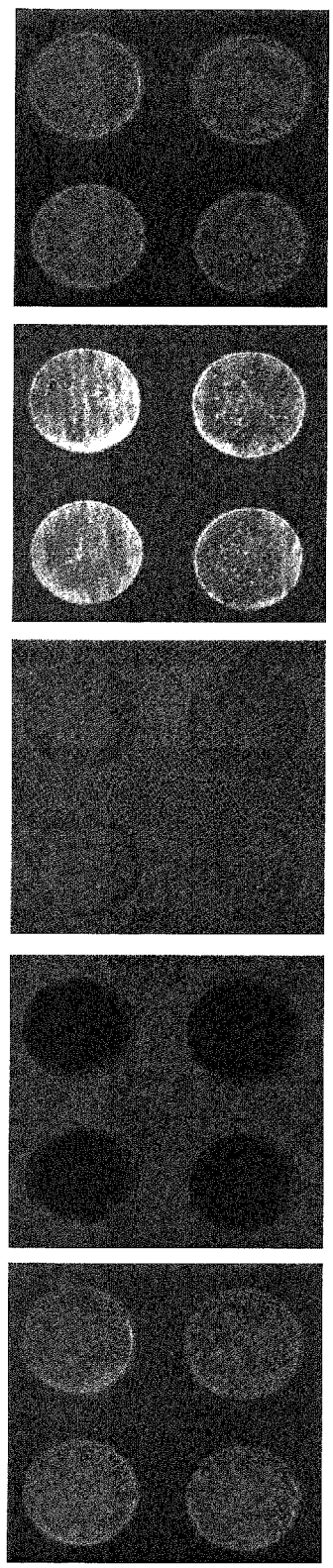
FIGS. 3(a)-3(e) are interference diagrams of five-step phase differences generated from an electro-optic modulator in accordance with the present invention.

FIG. 2 is a schematic diagram of an SPR microscope using common-path phase-shift interferometry in accordance with the present invention. A coherent light source emits coherent light as an incident light—He—Ne laser with a 632.8 nm wavelength for example. The coherent light goes through a linear polarizer 221, and the optical components of the incident light, including P-wave light and S-wave light, are adjusted. Afterwards, the polarized light is changed into a plane beam by a beam expender 23. The plane beam enters a coupler 24 (as a prism in the embodiment) to excite the interface between a second metal film 262 and a sample layer 80 to generate SPW.

Because the characteristic of Au is quite stable, it is suitable to take Au with a dielectric constant of −10.8+1.47j at 632.8 nm as the second metal film 262. When Cr is taken as the material of the first metal film 261 for the sake of interface compensation, the adhesive force between the coupler 24 and the second metal film 262 gets stronger. Furthermore, if the second metal film 262 and the coupler 24 adhere well to each other without any medium, the second metal film 262 can be coated directly on the surface of the coupler 24.

After being reflected from the prism, the P-wave and S-wave light, having phase differences between them, pass through an electro-optic modulator (EOM) 25 and a focusing lens 28. A beam splitter 27 divides the beam into two portions. The electro-optic modulator 25 is identical to a liquid crystal phase retarder or an electro-optic crystal such as $LiNbO_3$, $ADP(NH_4H_2PO_4)$, or $KPD(KH_2PO_4)$. The fluctuation direction of the P-wave occurs along a fast axis and the S-wave along a slow axis. The phase delay of the S-wave light is modulated by the external voltage applied to the modulator to change the direction of its polarization axis. After modulation, the P-wave and S-wave of the straight light beam are directed through a polarizer 223, and then interference between them occurs simultaneously. Finally, an image camera 29 captures the corresponding interference diagrams. The S-wave light of the redirected light beam is filtered by a polarizer 222, hence only the P-wave light goes into a photo-detector 2a capable of detecting a resonance angle.

It is preferable to use a liquid crystal phase retarder to have common-path phase-shift interference because the retarder is identical to a positive-type crystal with a single light axis. In comparison with other electro-optic crystals, the retarder has the advantages of ease of manufacture, low operating voltage, and low cost. Furthermore, the anisotropic index of the retarder is far bigger than those of the common electro-optic crystals.

By means of changing the external voltage, the phase difference between the fast and slow axes also varies. For example, after calibration, five voltage values obtained can yield phase differences of $\theta_0$, $\theta_0+\frac{1}{2}\pi$, $\theta_0+\pi$, $\theta_0+\frac{3}{2}\pi$ and $\theta_0+2\pi$, wherein $\zeta_0$ is an initial phase difference. From these phase differences, five different interference diagrams can be obtained, and then a continuous distribution diagram of phase variation can be reconstructed from the five interference diagrams by using a phase reconstruction method.

In order to bind the probe DNA on the thin gold film slide, the slide was immersed in a 1-mM thiol solution (HS$(CH_2)_{15}$COOH) for six hours and then placed in a solution with 1 mg/ml N-ethyl-N-(3-dimethylaminopropyl) carbodiimide hydrochloride (EDC hydrochloride, FLUKA) in 40 mM 2-(N-morpholino) ethanesulfonic acid (MES) for a further 6 hours. After cleaning the slide with deionized water and alcohol, the probe DNA was mechanically spotted in a matrix arrangement. Finally, a blocking solution (methanol) was applied to modify the functional group of thiol —COOH into —$CH_3$ to prevent the target DNA from being captured on the free thiol/EDC area. FIGS. 3(a)-3(e) present five interference frames of the four 15-mer ssDNA (single-stranded DNA) spots (5'-CATCCGTGTGGTAAC-3') captured by a 1.0×1.0 $mm^2$ area-scan CCD camera with 50×50 pixels. Each spot has a diameter of approximately 200 μm and the pitch between consecutive probe ssDNA spots is 500 μm. If the sensing area includes a ssDNA spot, local variations of the interference pattern can be observed.

Figure 4:
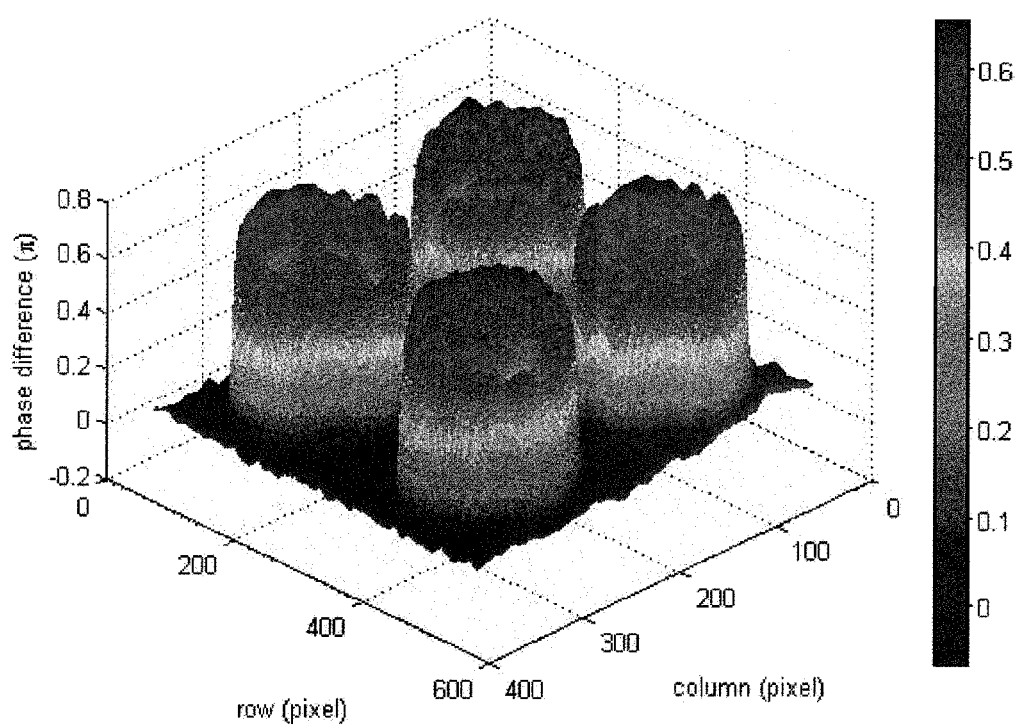
FIG. 4 is a phase distribution diagram reconstructed from the interference diagrams of five-step phase differences in accordance with the present invention.

FIG. 4 presents the reconstructed phase jump associated with the four probe ssDNA spots. The phase difference between the areas with and without DNA is seen to be approximately $0.57\pi$. The local resolution is $\pi/1000$, i.e. the size of the probe DNA spot. Hence, by maintaining a detection resolution of approximately 0.5 pg/$mm^2$ surface coverage of biomaterial, the screening area can simultaneously monitor up to 2,500 individual spots in a 10×10 $mm^2$ area.

Figure 5:
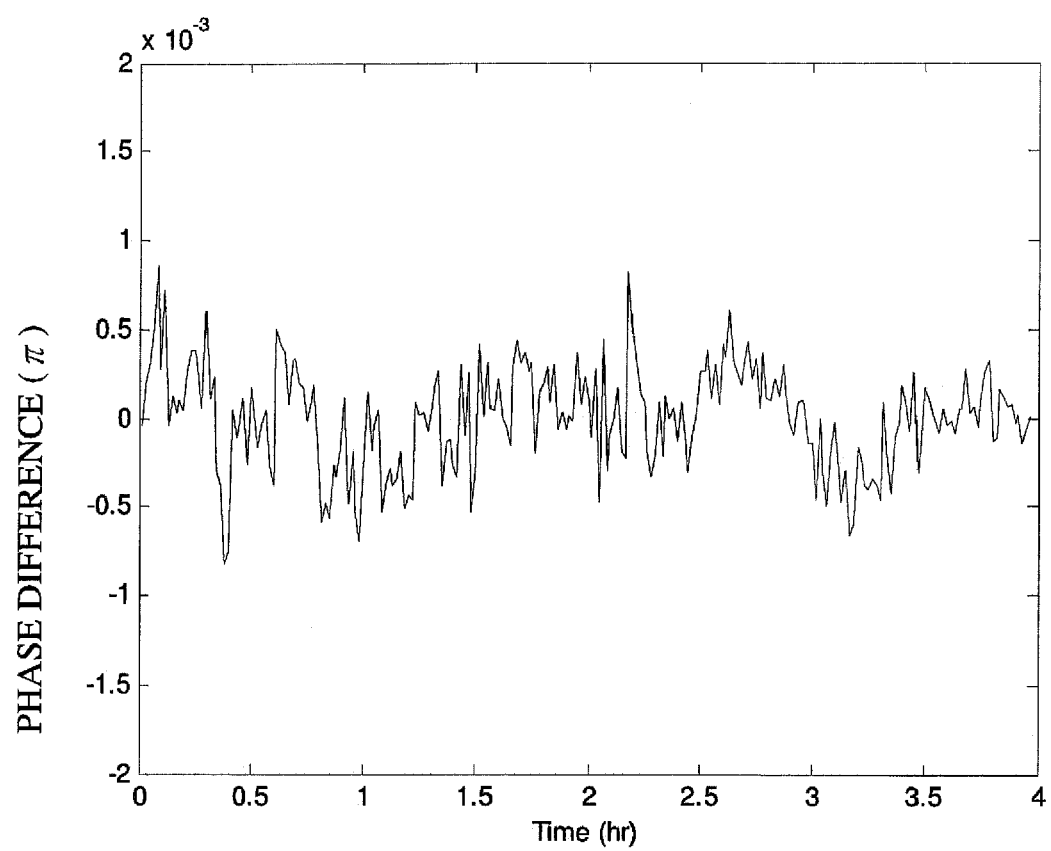
FIG. 5 is a graph of the stability of an SPR microscope in accordance with the present invention.
Figure 6:
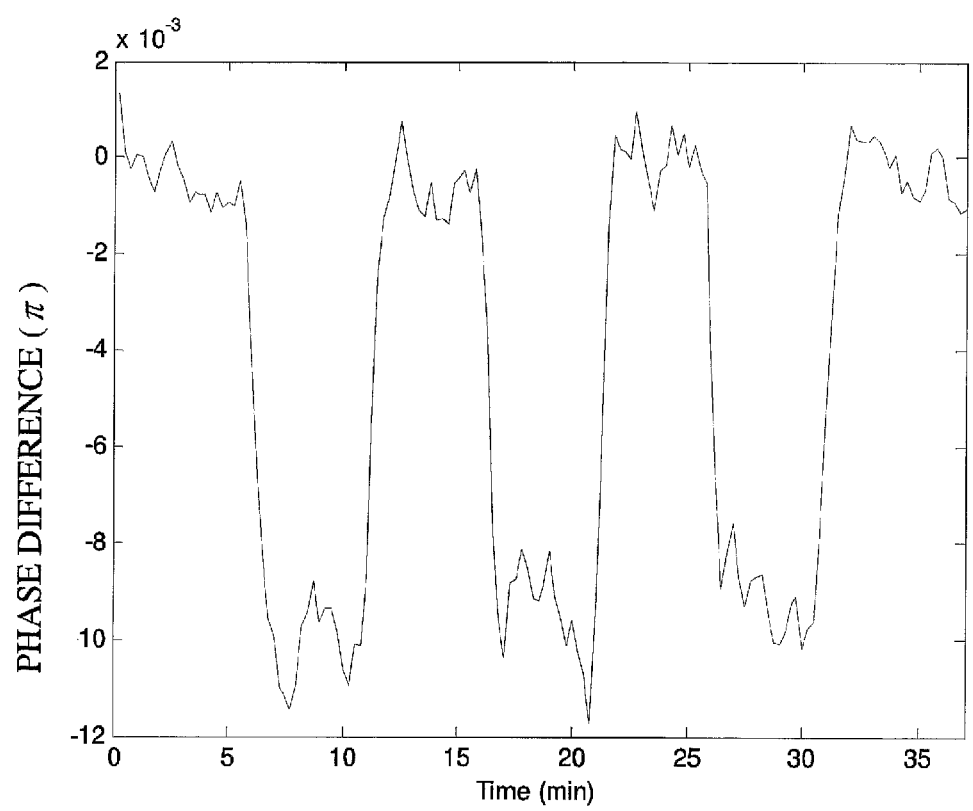
FIG. 6 is a graph of the sensitivity of an SPR microscope in accordance with the present invention.

In testing the system phase stability, the incident angle was adjusted to the SPR angle and nitrogen gas was used as the buffer sample with a flow rate of 100 μl/min and a constant temperature of 30° C. As shown in FIG. 5, the long-term phase stability was found to be $2.5 \times 10^{-4}\pi$ rms over four hours. To evaluate the detection limit of the system, the incident angle was adjusted to the SPR angle and the sample was alternated between nitrogen and argon gas every five minutes with a constant flow rate of 100 μl/min and a temperature of 30° C. The refractive indices of nitrogen and argon are known to differ by $1.5 \times 10^{-5}$. The phase variation for a refractive index change of $1.5 \times 10^{-5}$ is found to be $10^{-2}\pi$, as shown in FIG. 6. With a short-term (<30 min) phase stability of $10^{-4}\pi$, the developed system is capable of resolving a two-dimensional refractive index change of approximately $2 \times 10^{-7}$ for sample variation when using a thin gold film of 47.5 nm thickness.

In summary, the SPR microscope 20 uses common-path phase-shift interferometry to solve the phase drift problem resulting from external environmental variety, mechanical vibration and light instability. The microscope is suitable for measuring the 2-dimensional variation of the phase perpendicular to the surface of an analyte.

The aforementioned descriptions of the present invention are intended to be illustrative only. Numerous alternative methods may be devised by persons skilled in the art without departing from the scope of the following claims.

What is claimed is:

1. A surface plasmon resonance microscope using common-path phase-shift interferometry, comprising:
   a coupler;
   a coherent light source emitting coherent light entering the coupler;
   a metal film whose one surface is adjacent to a sample layer, wherein the incident coherent light for the coupler excites the metal film so as to generate a surface plasmon wave from an interface between the metal film and the sample layer;
   an electro-optic modulator modulating the phases of light redirected from the coupler along different polarization directions; and
   an image camera capturing an interference diagram from the modulated light.

2. The surface plasmon resonance microscope using common-path phase-shift interferometry of claim 1, further comprising a polarizer placed between the coherence light source and coupler for adjusting polarization components of the coherent light.

3. The surface plasmon resonance microscope using common-path phase-shift interferometry of claim 2, further comprising a beam expender enlarging the coherent light from the polarizer to a plane beam.

4. The surface plasmon resonance microscope using common-path phase-shift interferometry of claim 1, further comprising a beam splitter dividing the modulated light through the electro-optic modulator into a straight portion and a redirected portion.

5. The surface plasmon resonance microscope using common-path phase-shift interferometry of claim 4, wherein the redirected portion is received by a photo-detector which detects a resonance angle of the surface plasmon wave as the straight portion enters the image camera.

6. The surface plasmon resonance microscope using common-path phase-shift interferometry of claim 5, further comprising a polarizer allowing P-wave light to pass through the polarizer and go into the photo-detector.

7. The surface plasmon resonance microscope using common-path phase-shift interferometry of claim 4, further comprising a focusing lens focusing the modulated light through the electro-optic modulator on the beam splitter.

8. The surface plasmon resonance microscope using common-path phase-shift interferometry of claim 4, further comprising a polarizer adjusting the components of the straight light along different polarization directions.

9. The surface plasmon resonance microscope using common-path phase-shift interferometry of claim 1, further comprising a phase reconstruction apparatus obtaining a plurality of interference diagrams from the image camera and reconstructing the interference diagrams as a two-dimensional phase distribution diagram which shows phase differences along a direction perpendicular to the interface between the metal film and the sample layer.

10. The surface plasmon resonance microscope using common-path phase-shift interferometry of claim 9, wherein the plurality of interference diagrams comprise five interference diagrams of five-step phase differences.

11. The surface plasmon resonance microscope using common-path phase-shift interferometry of claim 1, wherein the coupler is a prism.

12. The surface plasmon resonance microscope using common-path phase-shift interferometry of claim 1, wherein the coherent light source emits He-Ne laser light.

13. The surface plasmon resonance microscope using common-path phase-shift interferometry of claim 1, wherein the electro-optic modulator is a liquid crystal phase retarder, and phase differences of the coherent light along two of the polarization directions perpendicular to each other are adjustable by tuning an external operation voltage of the electro-optic modulator.

14. The surface plasmon resonance microscope using common-path phase-shift interferometry of claim 13, wherein the polarization directions perpendicular to each other are a fast axis and a slow axis.

15. The surface plasmon resonance microscope using common-path phase-shift interferometry of claim 1, wherein the metal film is made of Au.

16. The surface plasmon resonance microscope using common-path phase-shift interferometry of claim 15, further comprising another metal film of Cr which is placed between the metal film and the coupler.

17. The surface plasmon resonance microscope using common-path phase-shift interferometry of claim 1, wherein the metal film is coated on a surface of the coupler.

18. The surface plasmon resonance microscope using common-path phase-shift interferometry of claim 1, wherein the modulated light from the electro-optic modulator is decomposed into P-wave light and S-wave light respectively along the different polarization directions.

* * * * *